US008397553B2

(12) United States Patent
Xu et al.

(10) Patent No.: US 8,397,553 B2
(45) Date of Patent: Mar. 19, 2013

(54) LIQUID CHROMATOGRAPHY DETECTOR AND FLOW CONTROLLER THEREFOR

(75) Inventors: Zhi Xu, St. Louis, MO (US); Rakesh Bose, Wheeling, IL (US); James M. Anderson, Arlington Heights, IL (US)

(73) Assignees: The Curators of the University of Missouri, Columbia, MO (US); W.R. Grace & Co.-Conn, Columbia, MD (US)

( * ) Notice: Subject to any disclaimer, the term of this patent is extended or adjusted under 35 U.S.C. 154(b) by 476 days.

(21) Appl. No.: 12/517,946

(22) PCT Filed: Dec. 6, 2007

(86) PCT No.: PCT/US2007/086641
§ 371 (c)(1),
(2), (4) Date: Sep. 29, 2010

(87) PCT Pub. No.: WO2008/070776
PCT Pub. Date: Jun. 12, 2008

(65) Prior Publication Data
US 2011/0005305 A1    Jan. 13, 2011

Related U.S. Application Data

(60) Provisional application No. 60/868,926, filed on Dec. 6, 2006.

(51) Int. Cl.
*G01N 1/00* (2006.01)
(52) U.S. Cl. .............. 73/61.56; 73/48.61; 73/61.52; 73/51.55; 73/863.02; 73/863.03; 210/198.2; 210/656; 210/659; 210/662; 210/739; 422/70; 436/161

(58) Field of Classification Search .............. 73/48.61, 73/61.52, 61.55, 61.56, 863.02, 863.03; 210/198.2, 210/656, 659, 662, 739; 422/70; 436/161
See application file for complete search history.

(56) References Cited

U.S. PATENT DOCUMENTS

| 3,808,550 | A | | 4/1974 | Ashkin | |
|---|---|---|---|---|---|
| 3,894,562 | A | * | 7/1975 | Moseley, Jr. et al. | ........... 138/44 |
| 4,426,213 | A | * | 1/1984 | Stavropoulos | ........... 55/466 |

(Continued)

FOREIGN PATENT DOCUMENTS

| JP | 20070159377 | 6/1995 |
|---|---|---|
| JP | 2001296234 A | 10/2001 |

(Continued)

OTHER PUBLICATIONS

Koeniger, S.L., et al., "Development of Field Modulation in a Split-Field Drift Tube for High-Throughput Multidimensional Separations," J Proteome Res, 2005, 4:25-35.

(Continued)

*Primary Examiner* — Hezron E Williams
*Assistant Examiner* — Hoang Nguyen
(74) *Attorney, Agent, or Firm* — Senniger Powers LLP

(57) ABSTRACT

A flow controller for use with a liquid chromatography detector. The flow controller includes a flow channel comprising an inlet portion, a control channel portion in communication with the inlet portion, and an outlet portion in communication with said control channel portion. The control channel portion has a cross-sectional area smaller than a cross-sectional area of a drift tube of the liquid chromatography detector for channeling the flow of droplets through the smaller cross-sectional area. The flow controller is shaped and sized to reduce pressure fluctuations and turbulence in the droplet stream of the liquid chromatography detector.

30 Claims, 19 Drawing Sheets

U.S. PATENT DOCUMENTS

| | | | |
|---|---|---|---|
| 4,725,140 A | | 2/1988 | Musha |
| 4,941,618 A | * | 7/1990 | Hildebrand et al. ........... 239/432 |
| 4,958,529 A | * | 9/1990 | Vestal ........................ 73/864.81 |
| 5,061,065 A | | 10/1991 | Sommer |
| 5,529,244 A | | 6/1996 | Horvath, Jr. et al. |
| 5,581,081 A | | 12/1996 | Kato et al. |
| 5,837,826 A | | 11/1998 | Flickinger et al. |
| 5,872,622 A | | 2/1999 | Schildmeyer et al. |
| 6,024,129 A | * | 2/2000 | Schima ........................... 138/44 |
| 6,229,605 B1 | | 5/2001 | Benedict |
| 6,362,880 B1 | | 3/2002 | Anderson, Jr. et al. |
| 6,573,491 B1 | | 6/2003 | Marchitto et al. |
| 6,750,449 B2 | | 6/2004 | Marcus |
| 6,903,818 B2 | | 6/2005 | Cerni et al. |
| 7,006,218 B2 | | 2/2006 | Anderson, Jr. et al. |
| 7,114,525 B2 | * | 10/2006 | Krieger et al. ................... 138/44 |
| 7,268,881 B2 | | 9/2007 | Larsen et al. |
| 7,460,234 B2 | | 12/2008 | Larsen et al. |
| 7,500,479 B2 | * | 3/2009 | Nichols et al. ........... 128/200.23 |
| 7,760,355 B2 | * | 7/2010 | Larsen et al. ................. 356/335 |
| 7,841,336 B2 | * | 11/2010 | Rivera et al. ............. 128/200.21 |
| 7,911,609 B2 | * | 3/2011 | Jarrell ........................... 356/338 |
| 2001/0001575 A1 | | 5/2001 | Anderson, Jr. et al. |
| 2002/0186263 A1 | | 12/2002 | O'Connor et al. |
| 2005/0045239 A1 | | 3/2005 | Krieger et al. |
| 2007/0023037 A1 | | 2/2007 | Larsen et al. |

FOREIGN PATENT DOCUMENTS

| | | |
|---|---|---|
| JP | 20030222612 | 8/2003 |
| JP | 20066170689 A | 6/2006 |
| WO | 90/07132 | 6/1990 |
| WO | 9932174 A1 | 7/1999 |
| WO | 2004/077047 A1 | 9/2004 |
| WO | 2006083511 A2 | 10/2006 |

OTHER PUBLICATIONS

Nedelcu, O.T., et al., "Modeling of the Piezoelectric Micropump for Improving the Working Parameters," National Institute for Research and Development in Microtechnologies (IMT- Bucharest).

Gilson's 350 Micro Pump, Gilson Website: http//www.gilson.com/Products/product.asp?pID=28.

Sedex LT-ELSD brochure, Sedere Inc., Cranbury, N. J., 2004, 11 pages.

International Search Report and Written Opinion issued in PCT/US07186640, dated Aug. 22, 2008, 9 pages.

International Search Report and Written Opinion issued in PCT/US07/86641, dated May 16, 2008, 10 pages.

International Search Report and Written Opinion issued in PCT/US2009/047029, dated Aug. 3, 2009, 11 pages.

Charlesworth, John M., "Evaporative Analyzer as a Mass Detector for Liquid Chromatography", Analytical Chemistry, American Chemical Society, vol. 50, No. 11, Sep. 1, 1978, 7 pages.

Unknown, "SofTA Evaporative Light Scattering Detector", Internet Citation, Jul. 19, 2004, 1 page.

Van Nederkassel, a. M., "Development of a Ginkgo biloba fingerprint chromatogram with UV and evaporative light scattering detection and optimization of the evaporative light scattering detector operating conditions", Journal of Chromatography, Elsevier Science Publishers, vol. 1085, No. 2, Sep. 2, 2005, 10 pages.

Supplementary European Search Report dated Mar. 9, 2010 regarding European Patent Application No. 07854985.4, 7 pages.

Extended European Search Report dated Mar. 17, 2010 regarding European Patent Application No. 07865307.8; 9 pages.

* cited by examiner

LIQUID CHROMATOGRAPHY DETECTOR AND FLOW CONTROLLER THEREFOR

BACKGROUND

Evaporative light scattering detectors (ELSDs), mass spectrometers, and charged aerosol detectors are used routinely for Liquid Chromatography (LC) analysis. In such a device, a liquid sample is converted to droplets by a nebulizer. A carrier gas carries the droplets through a nebulizing cartridge, an impactor, and a drift tube. Conventional devices place the impactor in the path of the droplets to intercept large droplets, which are collected and exit the drift tube through an outlet drain. The remaining appropriately-sized sample droplets pass through the drift tube, which may be heated to aid in evaporation of a solvent portion of the droplets. As the solvent portion of the droplets evaporates, the remaining less volatile analyte passes to a detection cell, or detector, for detection according to the type of device utilized. In the detection cell of an ELSD, for example, light scattering of the sample is measured. In this manner, ELSDs, mass spectrometers, and charged aerosol detectors can be used for analyzing a wide variety of samples.

Conventional detection devices suffer from various drawbacks, including relatively high levels of jagged peak noise detected by the detection cell. Such excessive jagged peak noise can hamper the ability of the detection device to accurately measure the properties of the sample droplets and can decrease sensitivity overall. One conventional strategy for addressing the baseline noise issue of conventional detection devices is to include a diffuser trapping device for preventing large particles, which can increase background noise, from traveling through the drift tube to the detector. Such diffusers, however, are not capable of eliminating all noise. In addition, such diffusers may cause condensation in the drift tube and peak broadening under operating conditions of the detection device. Peak broadening is particularly troublesome for sharp peaks generated from Ultra Performance Liquid Chromatography (UPLC) where the width of a typical peak is between about 0.8 second and about 1.0 second. Therefore, such conventional detection devices with diffusers are unable to adequately reduce noise and increase sensitivity.

SUMMARY

The following simplified summary provides a basic overview of some aspects of the present technology. This summary is not an extensive overview. It is not intended to identify key or critical elements or to delineate the scope of this technology. This Summary is not intended to be used as an aid in determining the scope of the claimed subject matter. Its purpose is to present some simplified concepts related to the technology before the more detailed description presented below.

Accordingly, aspects of the invention provide a flow controller for a detection device that reduces pressure fluctuations in the droplet flow for decreasing noise and increasing sensitivity. The flow controller includes a flow channel having a cross-sectional area smaller than a cross-sectional area of the drift tube to decrease noise and increase sensitivity, while maintaining adequate signal strength. By reducing such noise, the detection device is capable of achieving a higher level of sensitivity.

BRIEF DESCRIPTION OF THE DRAWINGS

Corresponding reference characters indicate corresponding parts throughout the drawings.

DETAILED DESCRIPTION

Figure 1:
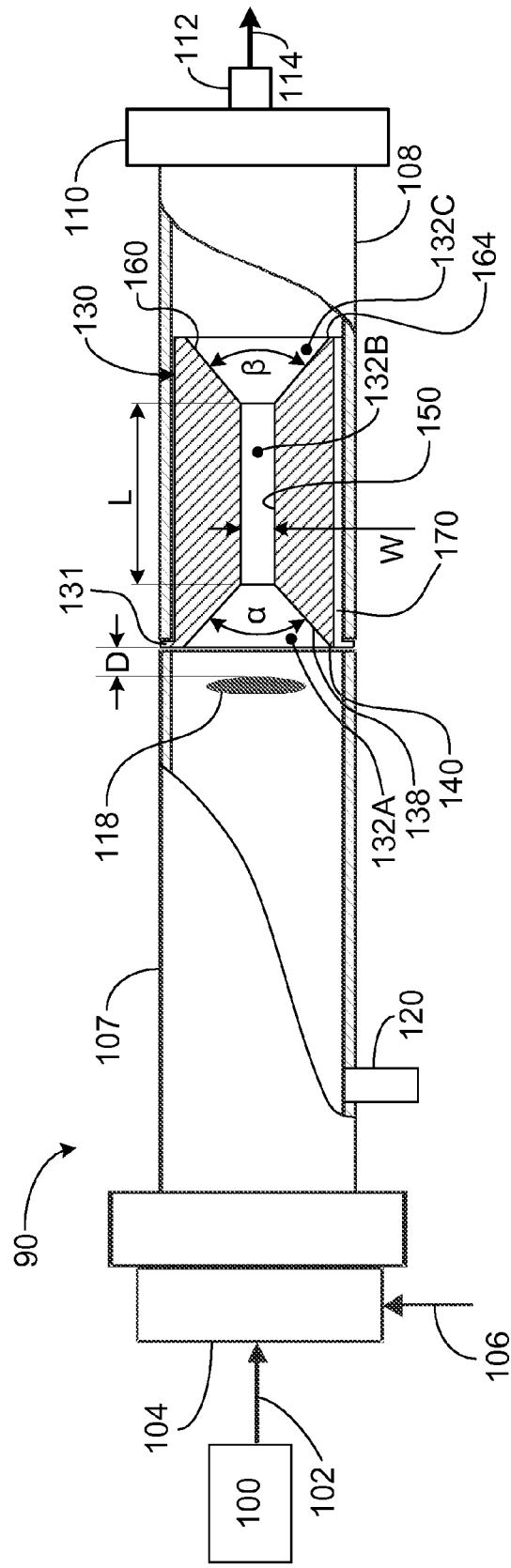
FIG. 1 is a schematic of an ELSD with a flow controller of one embodiment of the invention with portions partially broken away to reveal internal construction.

FIG. 1 illustrates an ELSD, generally indicated 90, according to one embodiment of the present invention. As would be understood by one skilled in the art, reference herein to exemplary embodiments of the invention applied to an ELSD are readily applicable to other detection devices, such as mass spectrometers and charged aerosol detectors, for example. A liquid chromatography (LC) column 100 provides effluent 102 (i.e., the mobile phase) to a nebulizer 104. The nebulizer also is provided with carrier gas 106, such as an inert gas (e.g., Nitrogen). As would be understood by one skilled in the art, the nebulizer 104 produces droplets, or a droplet stream, for analysis, which are carried through a nebulizing cartridge 107 and a drift tube 108 of the ELSD 90 by the carrier gas 106. Other mechanisms for moving the droplet stream through the apparatus, such as by an electric field or with a vacuum, may be utilized without departing from the scope of the exemplary embodiments of the invention. The droplets are generally within a size range of between about 10 micrometers (400 microinches) and about 100 micrometers (4 mils). For example, nebulized water droplets range from about 40 micrometers (1.6 mils) to about 60 micrometers (2.4 mils) as the droplets exit the nebulizer 104. In contrast, nebulized acetonitril droplets range from about 15 micrometers (590 microinches) to about 20 micrometers (790 microinches) as the droplets exit the nebulizer 104. Other compounds will form droplets of various size ranges, as would be readily understood by one skilled in the art.

As the carrier gas 106 and droplets flow through the nebulizing cartridge 107 and the drift tube 108, which can be heated, evaporation of the mobile phase 102 (solvent) occurs and the size of the droplets decreases. The gas stream continues by entering a detection cell 110 (e.g., an optical cell), which is the detection module of the unit. The stream passes through the detection cell 110 and out an exit port 112 as a waste gas steam 114. The detection cell 110 is adapted for receiving the droplets for analysis, as would be readily understood by one skilled in the art.

Referring now to FIGS. 1 and 2A-2C, the ELSD 90 additionally comprises an impactor 118 received within the nebulizing cartridge 107 adapted to intercept droplets larger than a particular size carried from the nebulizer 104 through the nebulizing cartridge 107 by the carrier gas 106. The droplets not intercepted are allowed to pass by the impactor 118 through open areas 119 formed between the impactor 118 and the nebulizing cartridge 107.

Figure 2A:
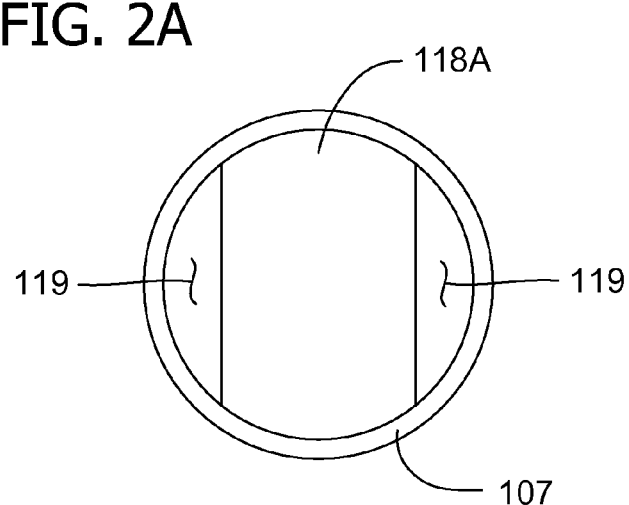
FIGS. 2A-2C are schematic end views of exemplary impactors received within nebulizing cartridges.
Figure 2B:
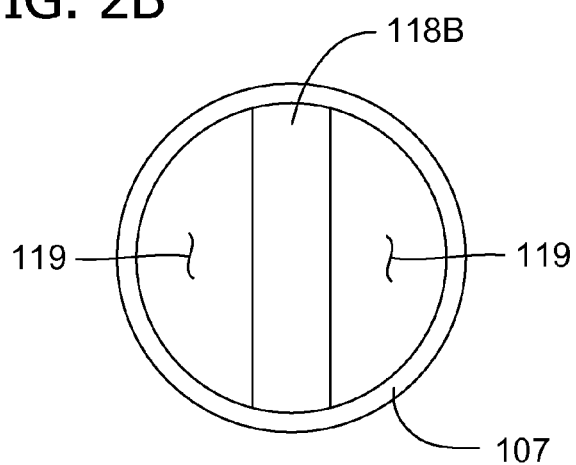

As would be readily understood by one skilled in the art, the specific shape, position, size, and configuration of the impactor 118 can be altered to control what size droplets are intercepted by the impactor and what portion of the droplet flow is allowed to pass through the open areas 119. For example, the exemplary impactor 118A depicted in FIG. 2A is larger than the exemplary impactor 118B depicted in FIG. 2B, thereby stopping more particles and forming smaller open areas 119 for flow. With the split-flow configuration of each of these exemplary impactors 118A, 118B, the impactor is placed inside the nebulizing cartridge 107 to control the splitting of the mobile phase 102. Smaller and more uniform particle size distribution is achieved in the mobile phase 102 aerosol by removing the larger droplets of the mobile phase prior to the heated drift tube 108. The amount of sample reaching the detection cell 110 depends upon the size, shape, and proximity of the impactor 118 to the nebulizer 104. The larger the size of the impactor 118, the more the mobile phase 102 splits. Once intercepted, the collected droplets exit the nebulizing cartridge 107 through an outlet drain 120, which can be positioned either upstream or downstream from the impactor 118. As would be understood by one skilled in the art, any material may be used for the impactor. In one exemplary embodiment, the impactor is formed from a chemically-stable material with low heat capacity, such as Teflon® surrounding a rigid core (e.g., a metal such as stainless steel).

Figure 2C:
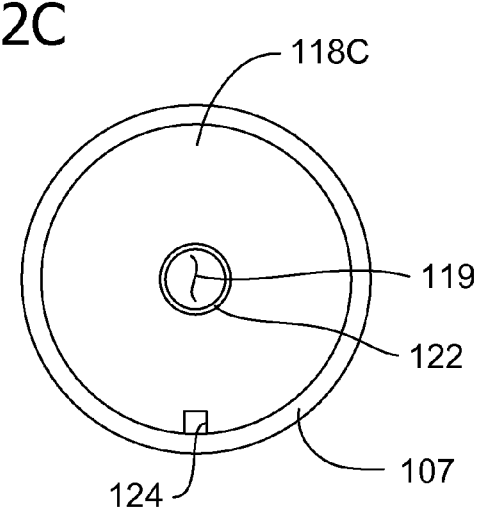

Referring now to FIG. 2C, a further exemplary embodiment of the impactor 118C is disclosed. Like the previous impactors 118A, 118B, this design also splits the mobile phase 102. This impactor includes a disc, also indicated 118C, that acts as an impactor for the mobile phase 102. The impactor 118C also includes a tube 122 extending generally perpendicular to the center of the disc with a distal end facing the nebulizer 104. In this position, the tube 122 intercepts the central portion of the mobile phase as it passes through the nebulizing cartridge 107. This portion of the mobile phase 102 comprises primarily laminar flow, whereby the portion of the mobile phase not striking the disc 118C of the impactor has relatively low turbulence. This selection of the portion of the mobile phase 102 having laminar flow facilitates a reduction in signal noise. The distal end, or inlet portion, of the tube 122 facing the nebulizer 104 is roughened to prevent any liquid from dripping across the inlet of the tube. The disc 118C of the impactor also includes a notch 124 directed downwardly inside the nebulizing cartridge 107 whereby liquid condensation within the nebulizing cartridge can flow past the impactor and reach the outlet drain 120. In one exemplary embodiment, the tube 122 extends from the disc 118C between about 1 and about 1.5 times the diameter of the nebulizing cartridge 107. In one example, the tube 122 extends about 28 millimeters (1.1 inches). In another exemplary embodiment, the tube 122 has an inner diameter of between about 20 percent and about 25 percent of the diameter of the nebulizing cartridge 107. In one example, the tube 122 has an inner diameter of about 5 millimeters (0.2 inch). Although the disc 118C and tube 122 may be formed from any materials, in one exemplary embodiment the disc is formed from a chemically-stable material with low heat capacity (e.g., Teflon®), and the tube is formed from a metal (e.g., stainless steel).

Referring again to FIG. 1, an exemplary embodiment of a flow controller of the present invention is generally indicated at 130. The flow controller includes a circumferential flange 131 for mounting the flow controller between the nebulizing cartridge 107 and the drift tube 108. The flow controller includes a flow channel 132 extending from one end of the flow controller to the other. For the flow controller 130 depicted in FIG. 1, the flow channel 132 includes an inlet portion 132A, a control channel portion 132B, and an outlet portion 132C. As would be readily understood by one skilled in the art, the flow controller 130 may be formed from many types of materials, including metals, such as aluminum and stainless steel. Generally speaking, the flow channel 132 has a cross-sectional area smaller than the drift tube 108 for channeling the flow of carrier gas 106 and droplets through the smaller cross-sectional area. As will be explained in greater detail below, the flow controller 130 is shaped and sized to reduce pressure fluctuations and turbulence in the droplet stream.

The inlet portion 132A includes a tapered inlet sidewall 138 extending from an open mouth 140 of the flow controller 130 and narrowing to the size and shape of the cross-section of the control channel portion 132B. In the embodiment shown, the tapered inlet sidewall 138 is substantially conical in shape and extends at an angle α measured between opposite sides of the tapered inlet sidewall. In one exemplary embodiment, angle α is between about 30 degrees and about 120 degrees. In other exemplary embodiments, the angle α is one of about 30 degrees, about 60 degrees, about 82 degrees, about 90 degrees, about 100 degrees, about 110 degrees, and about 120 degrees. Other α angles between about 30 degrees and about 120 degrees not specifically mentioned here may also be utilized without departing from the scope of the present invention. As would be readily understood by one skilled in the art, different α angles may provide different levels of noise reduction, depending upon other parameters of the ELSD 90. As such, modeling and/or experimentation may be required to optimize noise reduction for a particular ELSD apparatus 90.

The control channel portion 132B of the flow controller 130 comprises a generally cylindrical passage 150. In the embodiment shown, the cylindrical passage 150 is substantially circular. Other cross sectional shapes for the cylindrical passage 150 (e.g., elliptical) are also contemplated as within the scope of the present invention. The length L and width W, or diameter, of the control channel portion 132B may be selected to change the flow dynamics of the droplets as they pass through the flow controller 130. In one exemplary embodiment, the length L of the control channel portion 132B is sized between about 13 millimeters (0.5 inch) and about 25 millimeters (1 inch). In another exemplary embodiment, the width W, or diameter, of the control channel portion 132B is sized between about 3 millimeters (0.1 inch) and about 10 millimeters (0.4 inch). Other lengths L and widths W not specifically mentioned here may also be utilized without departing from the scope of the present invention. As would be readily understood by one skilled in the art, different combinations of lengths L and widths W may provide different amounts of noise reduction, depending upon the other parameters of the ELSD 90. As such, some modeling and/or experimentation may be required to optimize noise reduction for a particular ELSD apparatus 90.

The control channel portion 132B can also be defined according to the ratio of the length L to the width W. In one exemplary embodiment, the L/W ratio of the control channel portion 132B is between about 1.5 and about 20. In another exemplary embodiment, the L/W ratio of the control channel portion 132B is between about 2 and about 5. The control channel portion 132B of the flow controller 130 can also be defined according to the ratio of the cross-sectional area of the control channel portion 132B to the cross sectional area of the drift tube 108. When expressed as a percentage, this ratio indicates the flow area of the flow controller 130 as a percentage of the flow area of the drift tube 108. In one exemplary embodiment, this ratio is between about 2 percent and about 20 percent. In other words, the cross-sectional area of flow of the flow controller 130 is between about 2 percent and about 20 percent the size of the flow area of the drift tube 108. In another exemplary embodiment, the cross-sectional area of flow of the flow controller 130 is between about 3 percent and about 10 percent the size of the flow area of the drift tube 108. In still another exemplary embodiment, where the drift tube 108 has an inside diameter of about 22 millimeters (0.9 inch) and the control channel portion 132B of the flow controller 130 has an inside diameter of about 5 millimeters (0.2 inch), the cross-sectional area of flow of the flow controller is about 5 percent the size of the flow area of the drift tube.

The outlet portion 132C of the flow controller 130 also includes a tapered outlet sidewall 160 extending from the cross-section of the control channel portion 132B to an open exit 164 of the flow controller. In the embodiment shown, the tapered outlet sidewall 160 is substantially conical in shape and extends at an angle β measured between opposite sides of the tapered outlet sidewall. In one exemplary embodiment, angle β is between about 30 degrees and about 120 degrees. In other exemplary embodiments, the angle β is one of about 30 degrees, about 60 degrees, about 82 degrees, about 90 degrees, about 100 degrees, about 110 degrees, and about 120 degrees. Other β angles between about 30 degrees and about 120 degrees not specifically mentioned here may also be utilized without departing from the scope of the present invention. As would be readily understood by one skilled in the art, different β angles may provide different levels of noise reduction, depending upon the other parameters of the ELSD 90. As such, some modeling and/or experimentation may be required to optimize noise reduction for a particular ELSD apparatus 90. It should also be noted that the angle α and the angle β of the flow controller 130 may be different from one another without departing from the scope of the embodiments of the present invention.

The flow controller 130 is adapted to reduce pressure fluctuations and turbulence in the droplet flow, which is believed to be a substantial cause of noise observed by the detection cell 110. Such noise is exhibited as jagged Gaussian peak shape in chromatographs, as will be explained in detail below with respect to FIGS. 3-7. Without the flow controller 130 described herein, the detection cell 110 detects this pressure fluctuation and turbulence in the droplet flow as increased signal noise.

Without being bound to a particular theory, it is believed that a low pressure region forms adjacent (e.g., above) the nebulizer 104 when a significant liquid flow is introduced into the nebulizer 104. It is believed that this low pressure region adjacent the nebulizer 104 causes an oscillation, or fluctuation, or turbulence, in the droplet flow. The pressure oscillation, or fluctuation, or turbulence, disturbs the laminar flow of the droplet flow. This disturbance can be reduced by changing the boundary condition of the droplet stream. In particular, it is believed that the flow controller 130 changes the boundary condition of the droplet stream, thereby reducing the signal noise detected by the detection cell 110. It is also believed that the flow controller 130 focuses the droplets of the droplet stream into the center of the control channel portion 132B of the flow controller, as at least a portion of the droplet flow fluctuation is believed to be spatial in nature. By focusing the droplets toward the center of the control channel portion 132B, this spatial component of fluctuation can be reduced. Moreover, it is also believed that increasing the length L of the control channel portion 132B will further focus the droplets toward the center of the flow channel 132, thereby further reducing the pressure fluctuation.

In addition to reducing turbulence and peak jaggedness, the flow controller 130 also acts as a secondary impactor and further splits a higher percentage of the mobile phase 102. Both the impactor 118 and the flow controller 130 cause the splitting. Thus, a significant amount of the sample with the mobile phase 102 can drain out of the ELSD apparatus 90. To minimize this loss of mobile phase 102, the size of the impactor 118 may be reduced (e.g., FIG. 2B). By reducing the size of the impactor 118, the loss in the amount of sample from having the flow controller 130 acting as a secondary impactor is reduced. This can help compensate for the sample loss from using the flow controller 130 with the impactor 118.

Over time, liquid can accumulate in the drift tube 108 between the flow controller 130 and the detection cell 110. To address this liquid accumulation, a drain channel 170 formed along the underside of the flow controller 130 extends the length of the flow controller and through the flange 131. This allows the accumulated liquid to flow past the flow controller 130 and flange to the drain 120 located between the nebulizer 104 and the flow controller.

As will be explained in greater detail below with respect to the examples of FIGS. 3-7, there is some signal loss associated with reducing the pressure fluctuation with the flow controller 130. In one exemplary embodiment, to reduce this signal loss, the distance D between the impactor 118 and the flow controller 130 can be increased. By increasing the distance D to between about 3 millimeters (0.1 inch) and about 5 millimeters (0.2 inch), the noise reduction is slightly reduced, but the signal loss is lessened considerably. In another exemplary embodiment, the size of the impactor 118 as compared with the nebulizing cartridge 107 can be adjusted to maintain a substantial noise reduction without a significant loss of signal level. For example, the impactor 118 may be of the type depicted in FIGS. 2A-2C.

In one exemplary embodiment, the flow controller 130 is removable from at least one of the nebulizing cartridge 107, the impactor 118, and the drift tube 108, such as for inspection, cleaning, and/or replacement. In another exemplary embodiment, the flow controller 130 may be integrally formed with at least one of the nebulizing cartridge 107, the impactor 118, and the drift tube 108.

Example 1

Figure 3A:
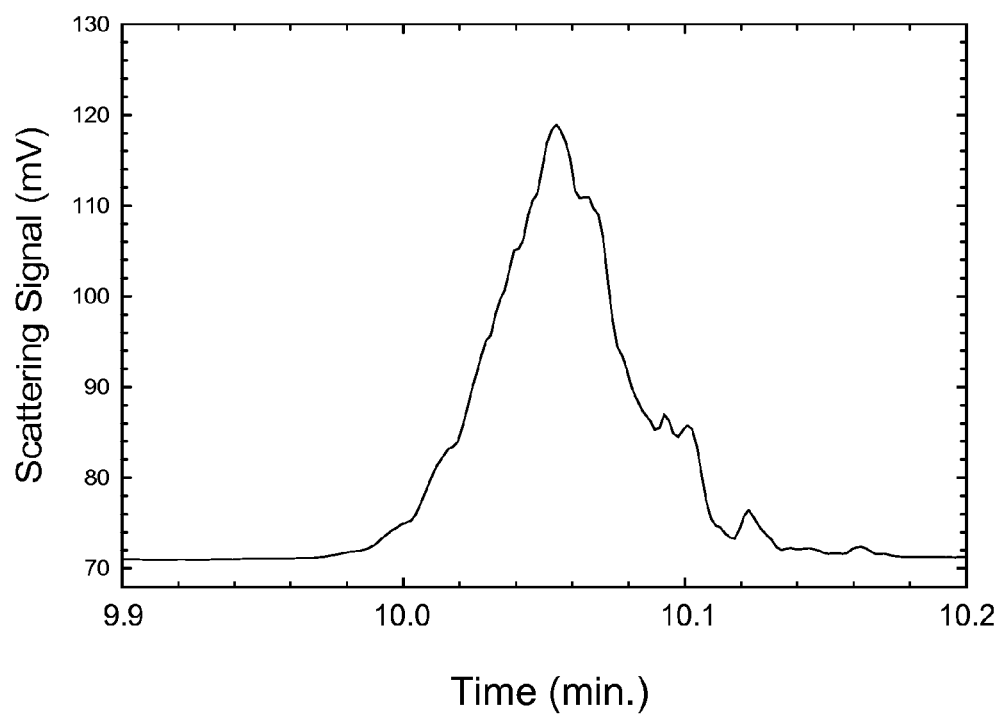
FIGS. 3A-3C are exemplary preamplifier chromatograms of 20 ppm Hydrocortisone without the flow controller of the present invention.
Figure 3B:
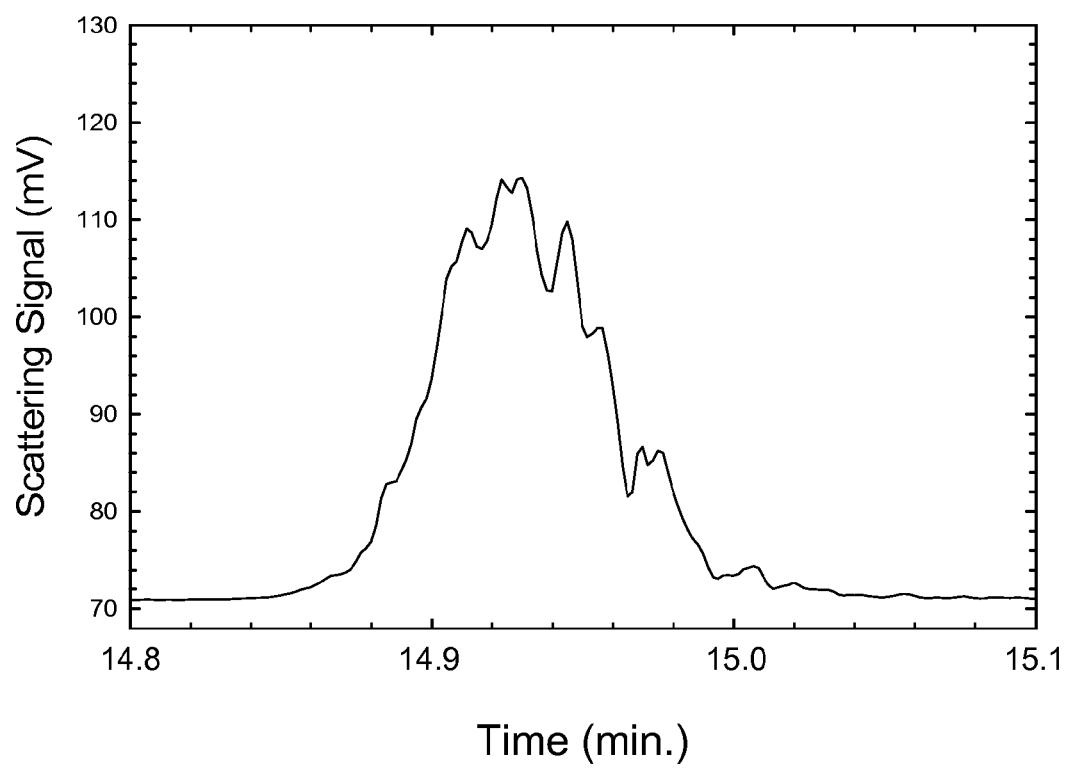
Figure 3C:
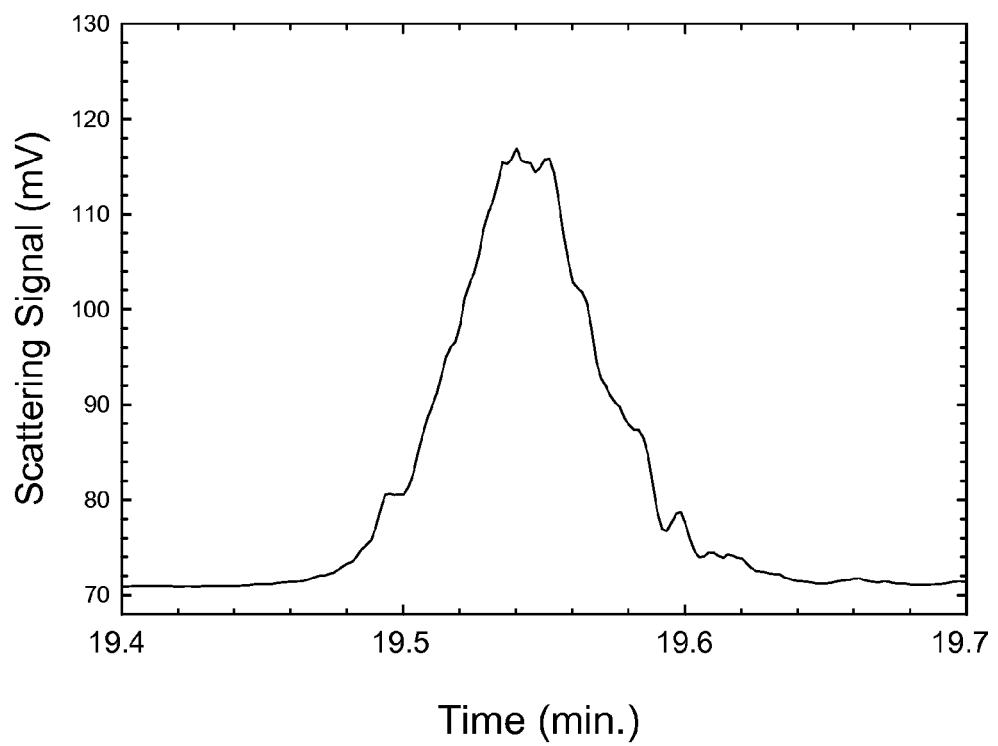

Referring now to FIGS. 3A-3C, preamplifier chromatograms of 20 ppm Hydrocortisone without the flow controller 130 of the present invention are depicted. These chromatograms demonstrate the noise associated with conventional ELSDs. Each of these chromatograms depicts the detected signal at a preamplifier of the ELSD, before any signal processing occurs. As would be readily understood by one skilled in the art, these jagged peaks reduce the overall sensitivity of the ELSD, as the peaks must be processed to remove the jagged peaks, thereby losing precision.

Figure 4A:
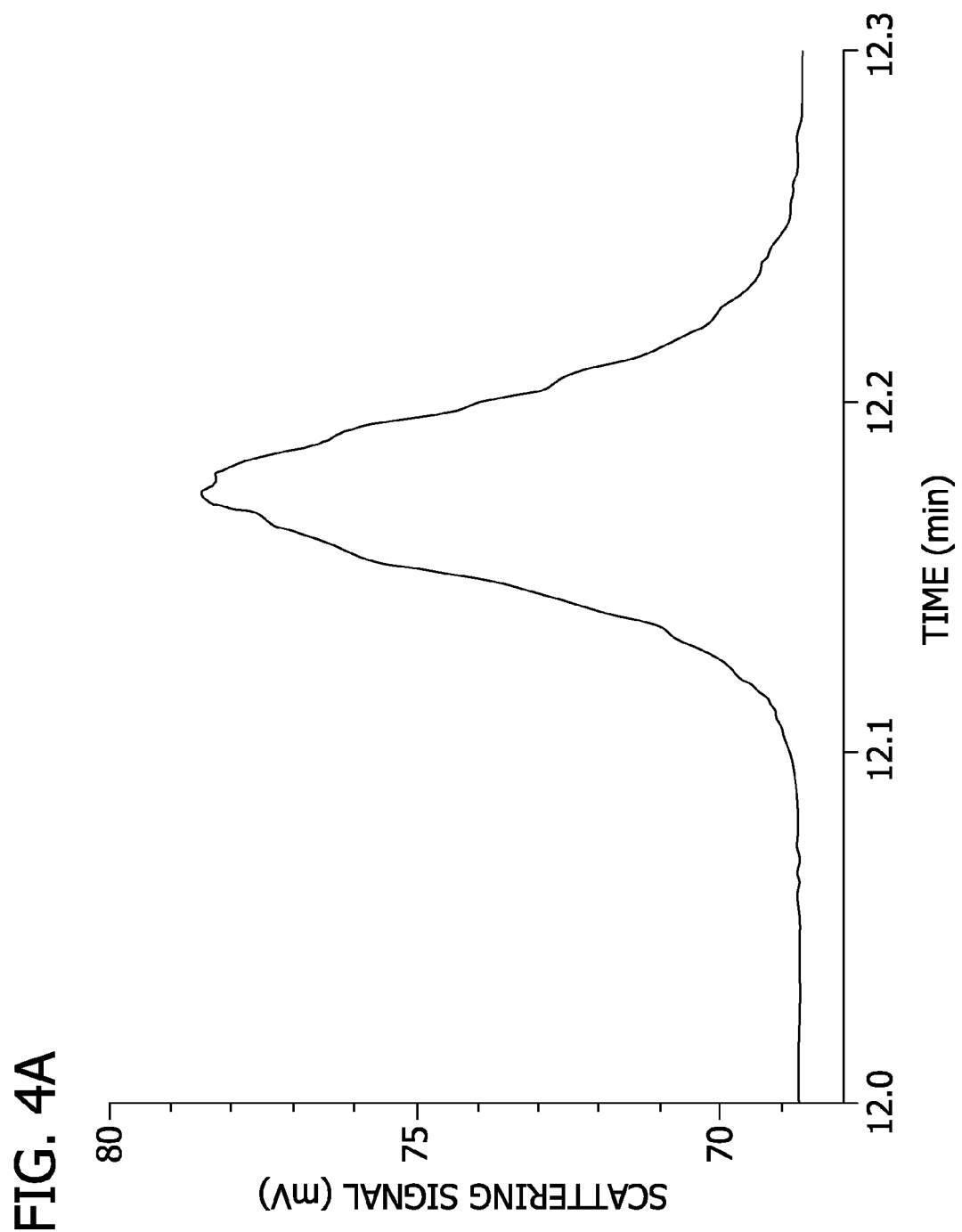
FIGS. 4A-4C are exemplary preamplifier chromatograms of 20 ppm Hydrocortisone with a flow controller adjacent the impactor.
Figure 4B:
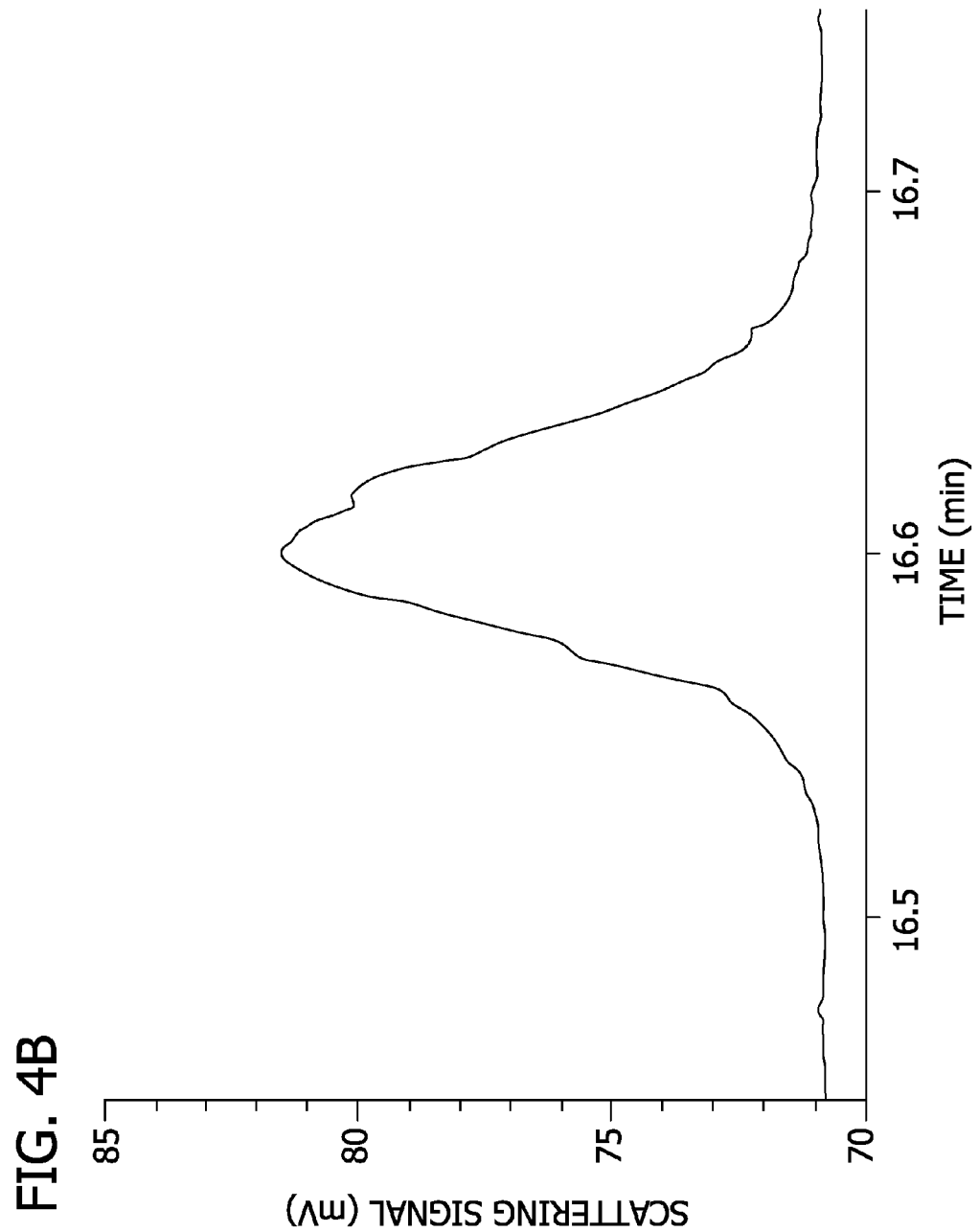
Figure 4C:
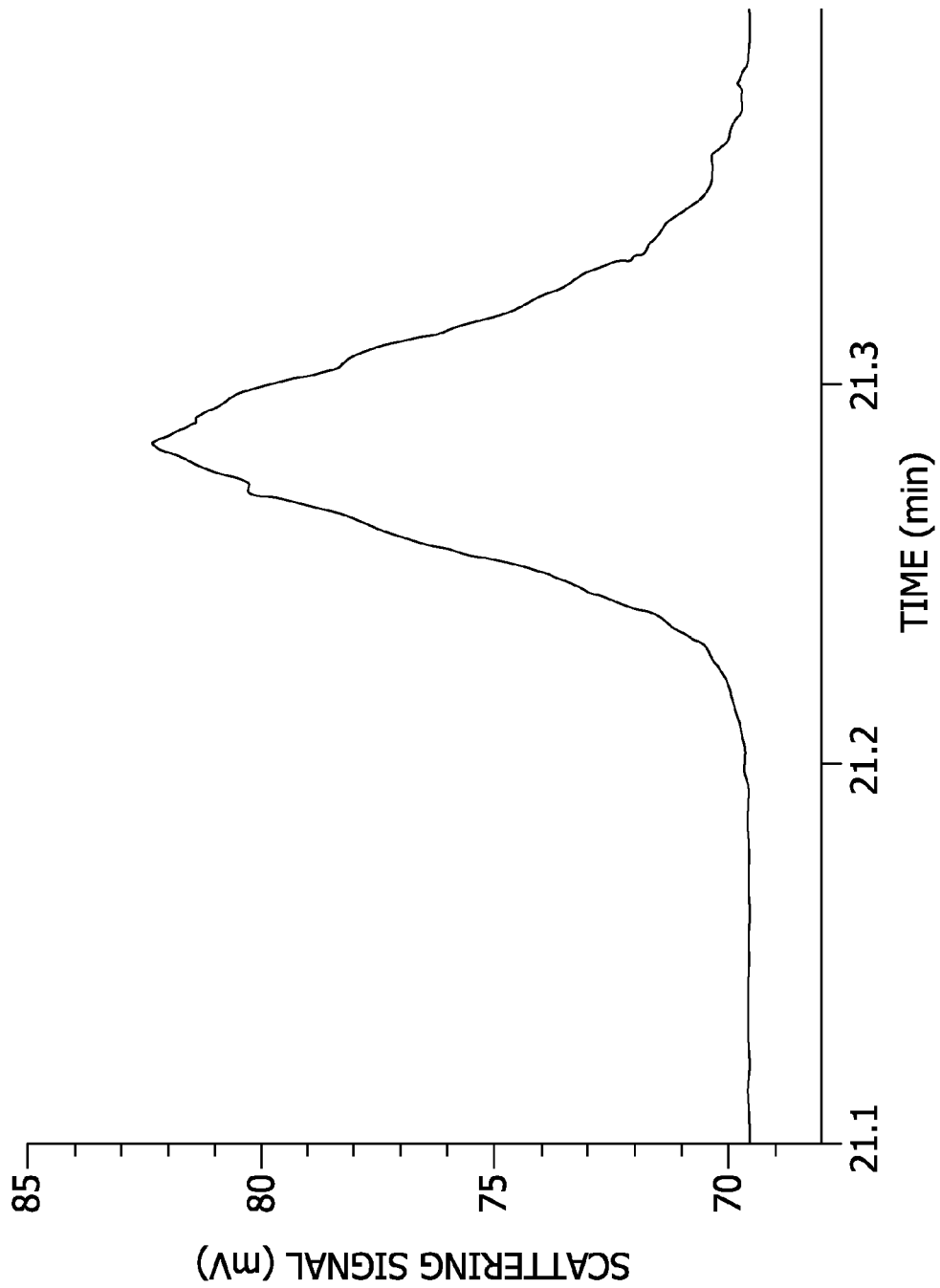

In contrast with the chromatograms of FIGS. 3A-3C, the preamplifier chromatograms of FIGS. 4A-4C for 20 ppm Hydrocortisone depict results with a flow controller 130 of the present invention adjacent the impactor 118. The signals of these chromatograms show a stark improvement over the signals of the chromatograms without the flow controller 130. Comparing FIGS. 3A and 4A, directly, for example, the signal with the flow controller 130 (FIG. 4A) is clearly less jagged than the signal without the flow controller (FIG. 3A). Direct comparisons between FIGS. 3B and 4B and FIGS. 3C and 4C reveal similar results. In each case, the addition of the flow controller 130 reduces noise over the conventional ELSD depicted in FIGS. 3A-3C. It should also be noted here that the signal strength measured by the detection cell 110 is reduced somewhat by the addition of the flow controller 130. Generally, the signal peak without the flow controller 130 is between about 110 millivolts and about 120 millivolts, with the baseline at about 70 millivolts. In contrast, with the flow controller 130, the signal peak is between about 75 millivolts and about 85 millivolts, with the baseline at about 70 millivolts.

Figure 5A:
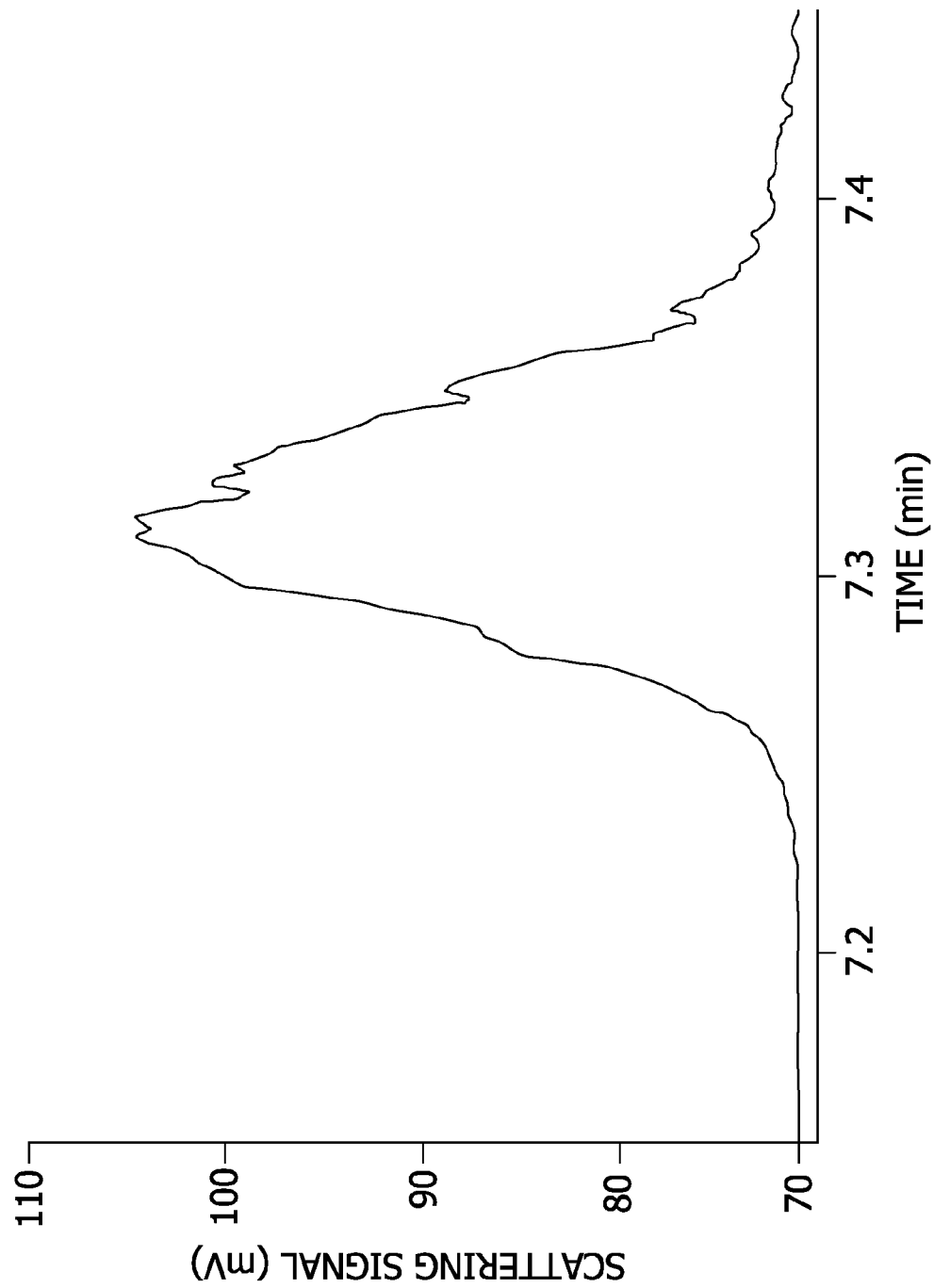
FIGS. 5A-5C are exemplary preamplifier chromatograms of 20 ppm Hydrocortisone with a flow controller arranged about 5 millimeters (0.2 inch) from the impactor.
Figure 5B:
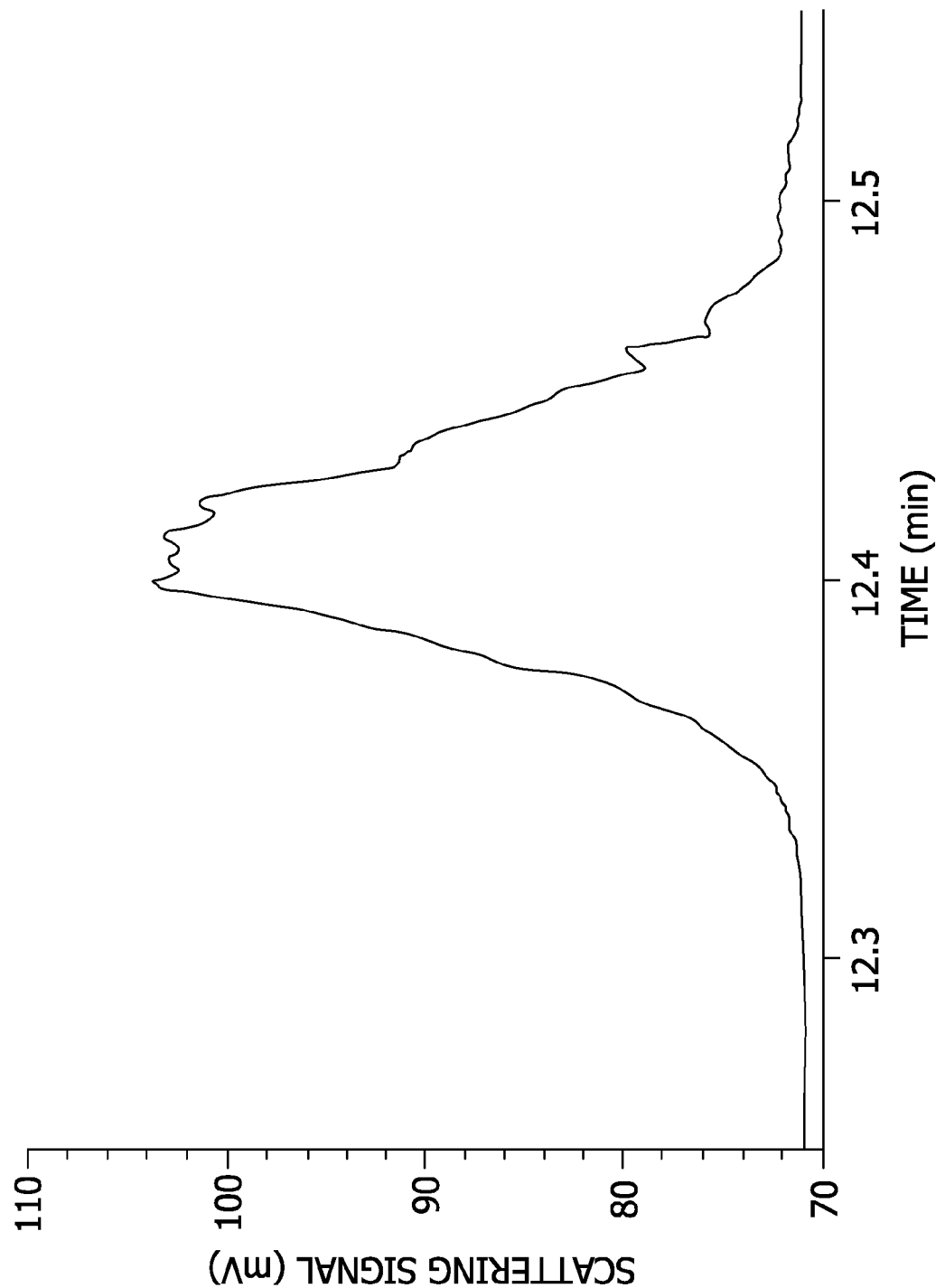
Figure 5C:
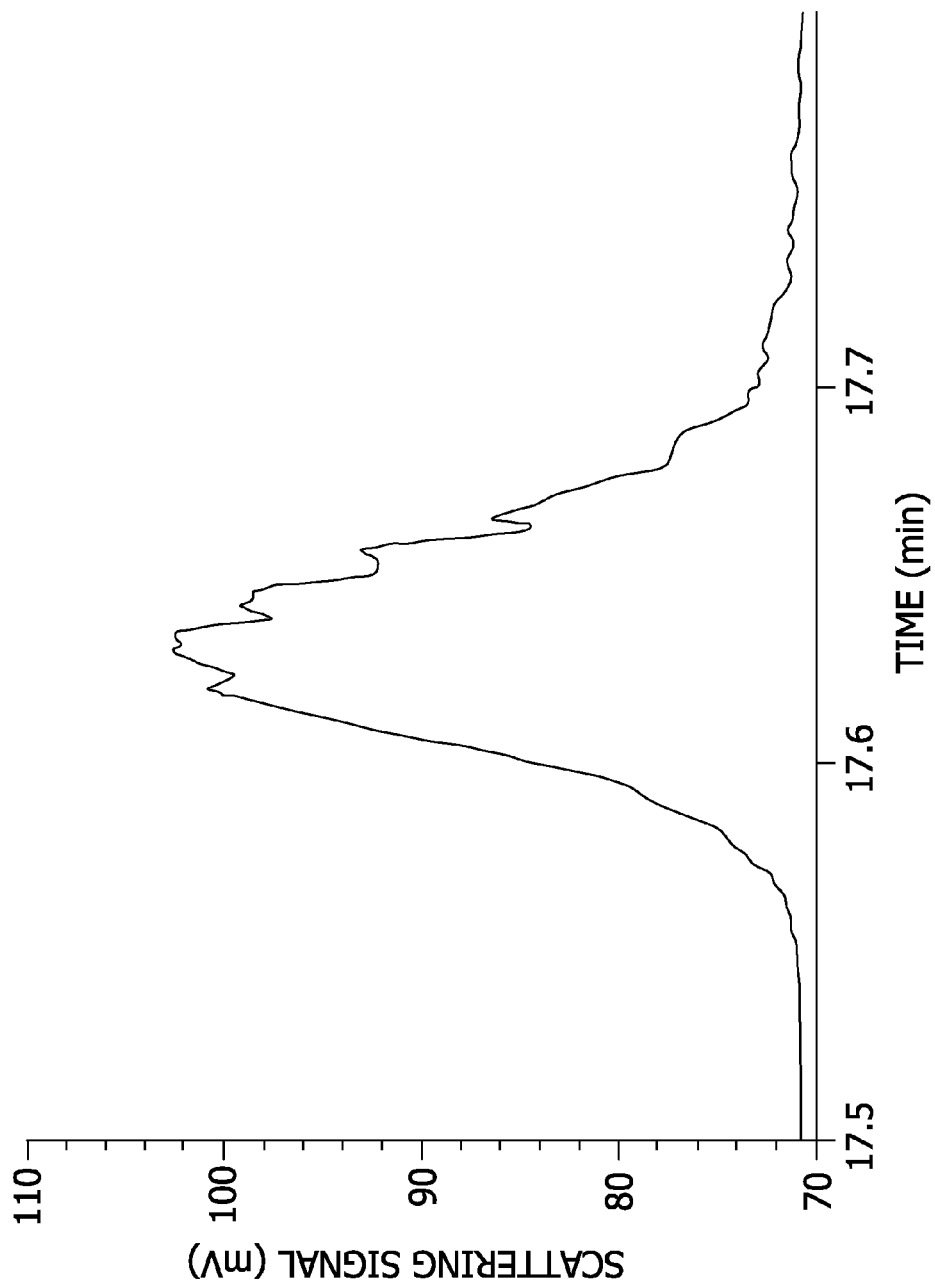

Referring now to FIGS. 5A-5C, chromatograms of 20 ppm Hydrocortisone with a flow controller 130 arranged about 5 millimeters (0.2 inch) from the impactor 118 are depicted. The distance of 5 millimeters (0.2 inch) refers to distance D as defined above and in FIG. 1. Here, the flow controller 130 is spaced from the impactor 118 in an effort to increase signal peak strength, while maintaining reduced noise over convention ELSD chromatographs (e.g., FIGS. 3A-3C). In each case, the addition of the flow controller 130 reduces noise over the conventional ELSD depicted in FIGS. 3A-3C, but increases the signal peak to between about 100 millivolts and about 110 millivolts, with the baseline at about 70 millivolts.

Example 2

Figure 6A:
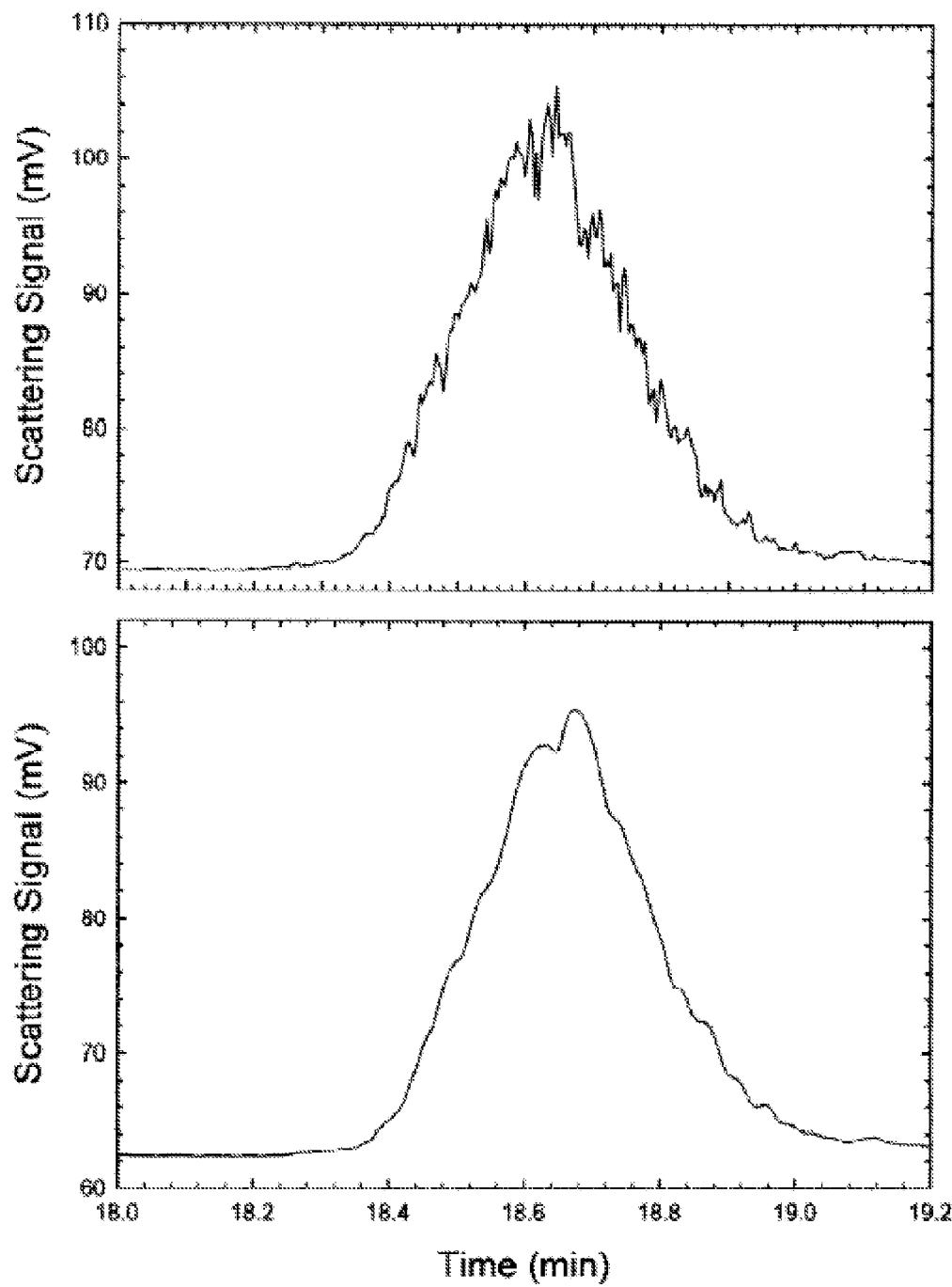
FIGS. 6A-6C are exemplary preamplifier and backpanel chromatograms of 0.18 mg/mL Ginkoglide B without the flow controller of the present invention.
Figure 6B:
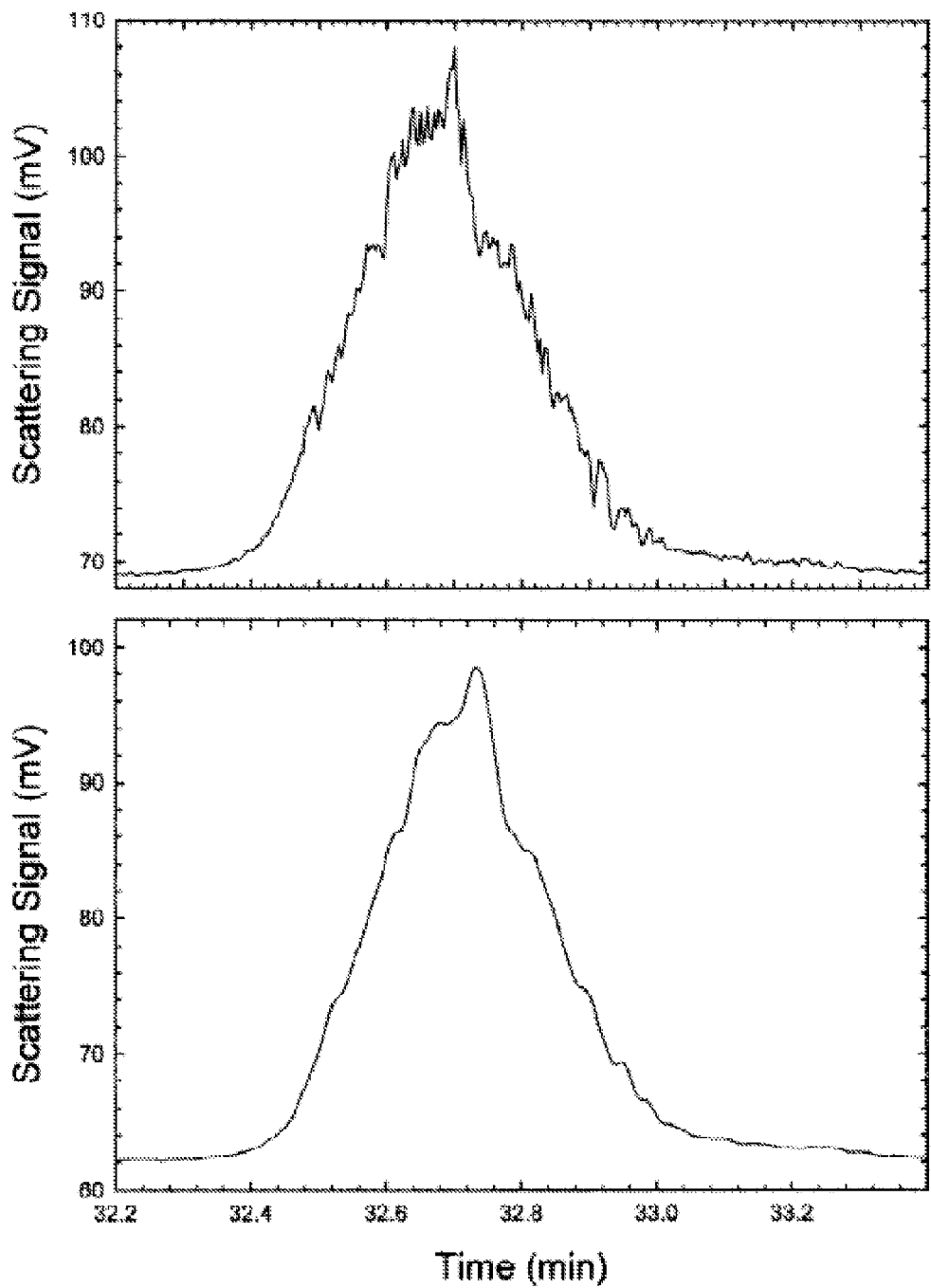
Figure 6C:
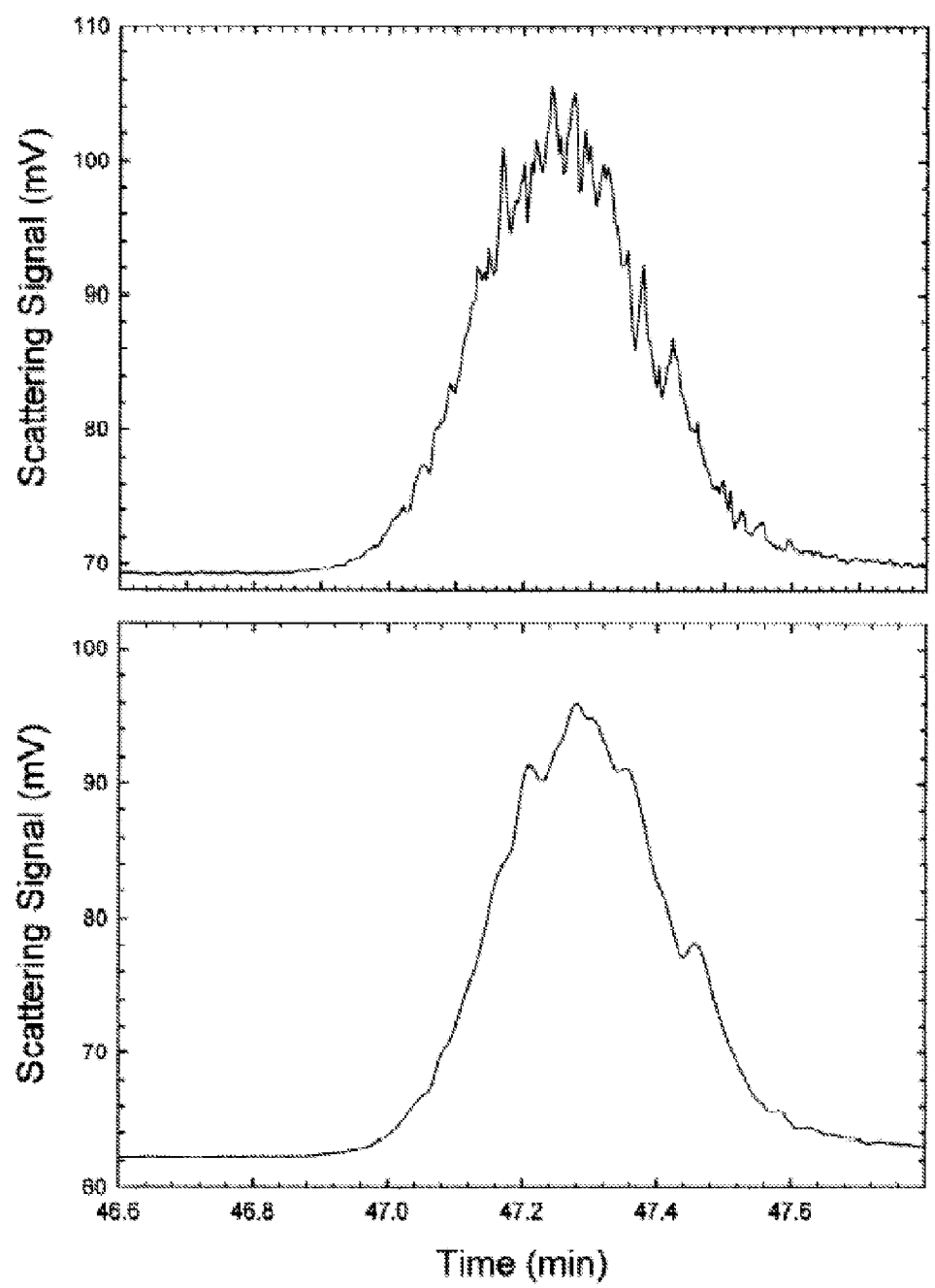

Referring now to FIGS. 6A-6C, exemplary preamplifier and backpanel chromatograms of 0.18 mg/mL Ginkoglide B without the flow controller of the present invention are depicted. The preamplifier chromatographs include substantial noise. Only after the signal is processed is some of the noise removed, as shown in the corresponding backpanel chromatographs. This processing, however, decreases the sensitivity of the ELSD and is not desirable. Moreover, even after the backpanel processing, the chromatographs still include substantial noise in each of FIGS. 6A-6C.

Figure 7A:
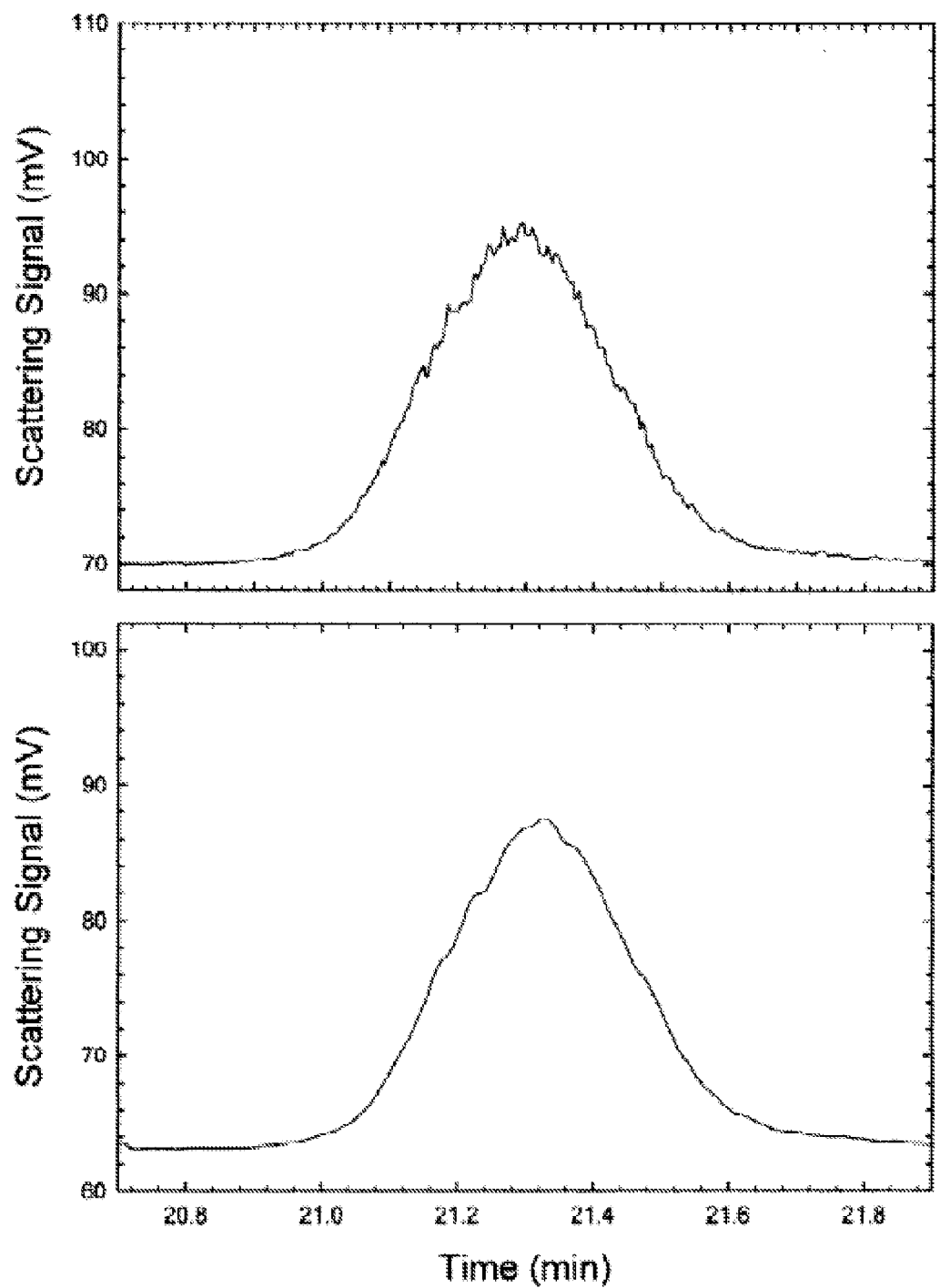
FIGS. 7A-7C are exemplary preamplifier and backpanel chromatograms of 0.18 mg/mL Ginkoglide B with a flow controller of the present invention.
Figure 7B:
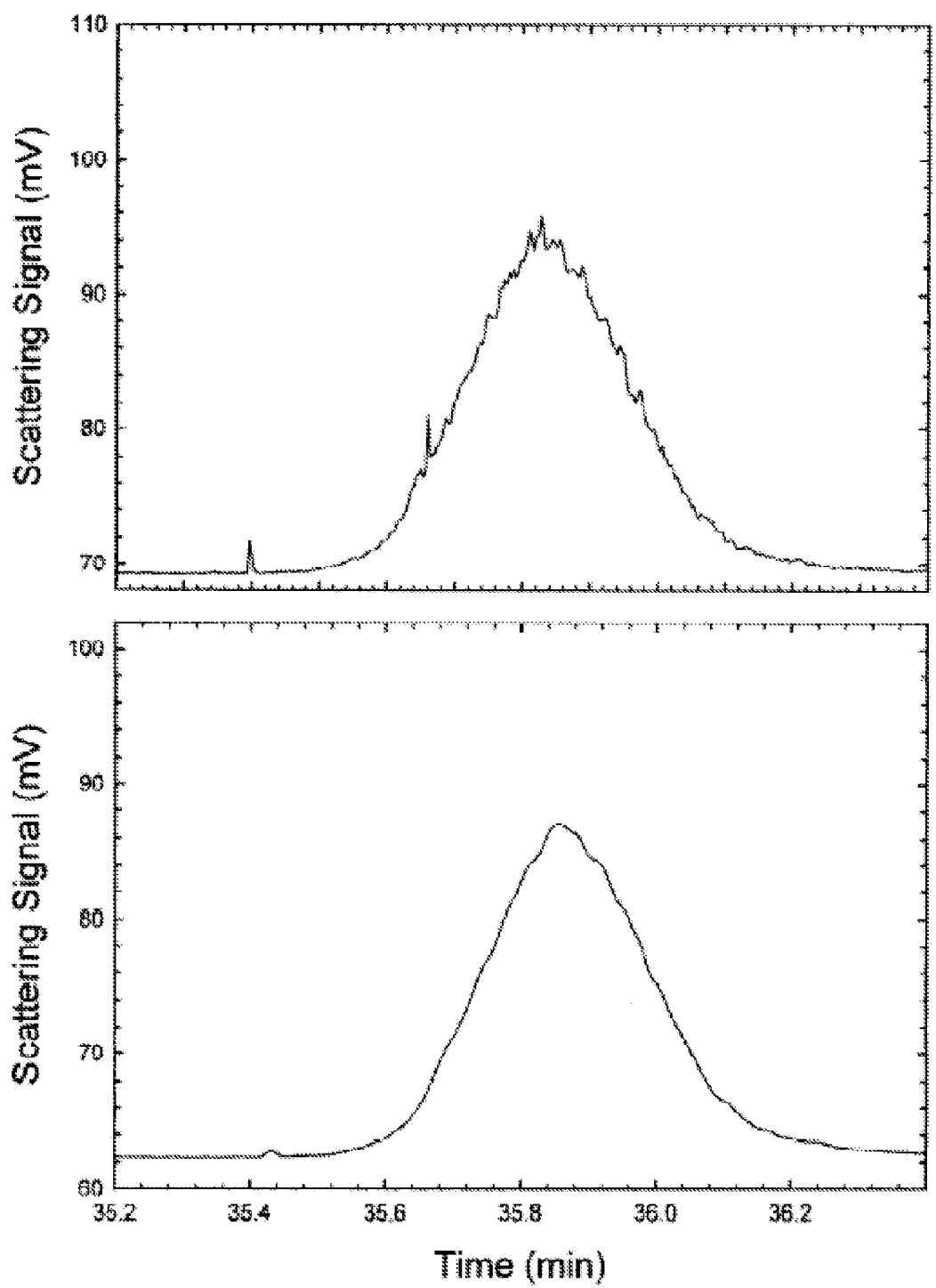
Figure 7C:
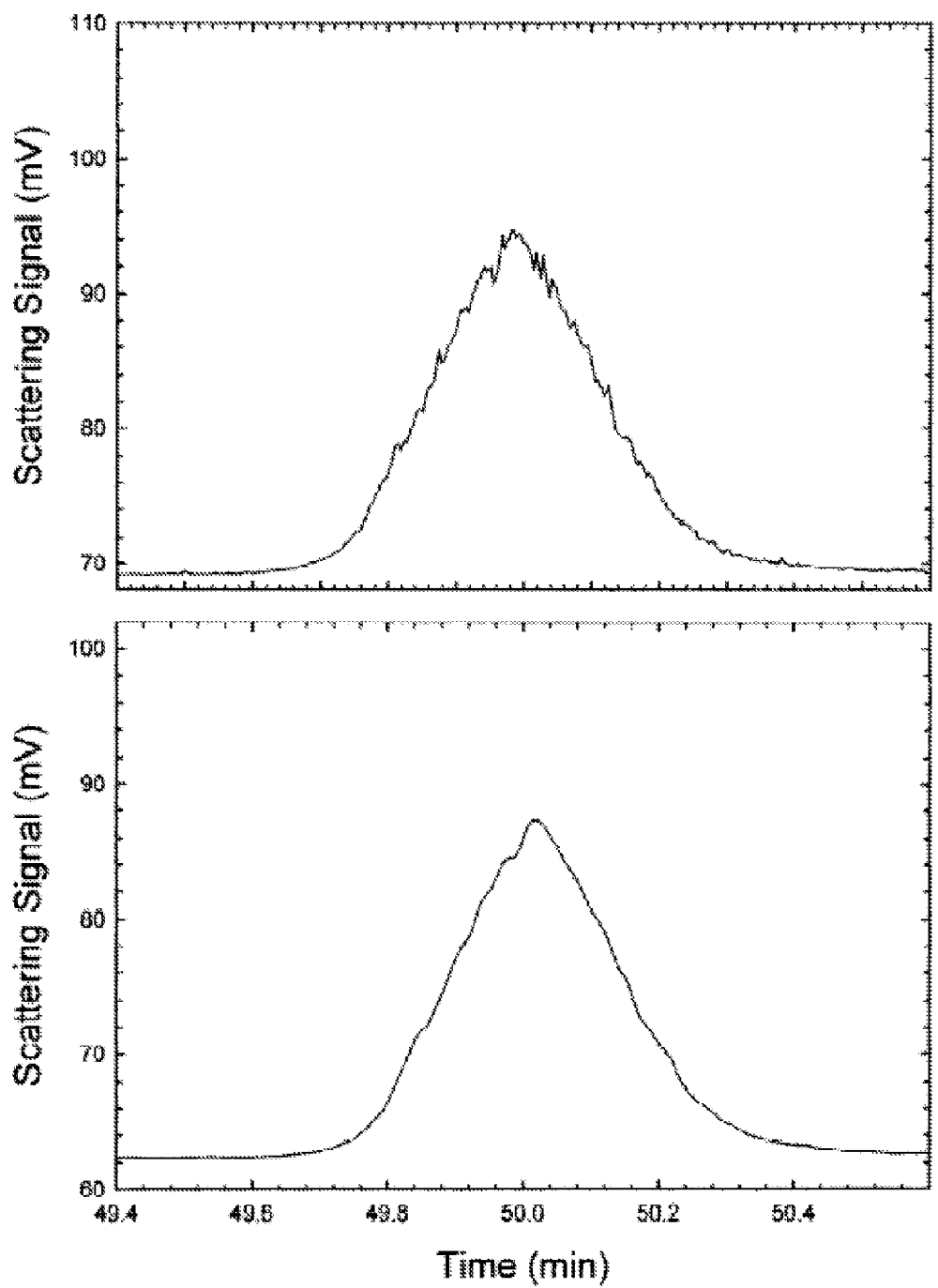

In contrast, FIGS. 7A-7C depict preamplifier and backpanel chromatograms of 0.18 mg/mL Ginkoglide B with a flow controller 130. These preamplifier chromatograms (FIGS. 7A-7C) are created with the flow controller 130 and exhibit significantly less noise than their counterpart chromatograms created without the aid of the flow controller (FIGS. 6A-6C). In particular, comparing FIGS. 6A and 7A, directly, for example, the signal without the flow controller 130 (FIG. 6A) is clearly more jagged and exhibits more noise than the signal with the flow controller (FIG. 7A) for both the preamplifier and backpanel chromatographs. Direct comparisons between FIGS. 6B and 7B and FIGS. 6C and 7C reveal similar results.

Figure 8:
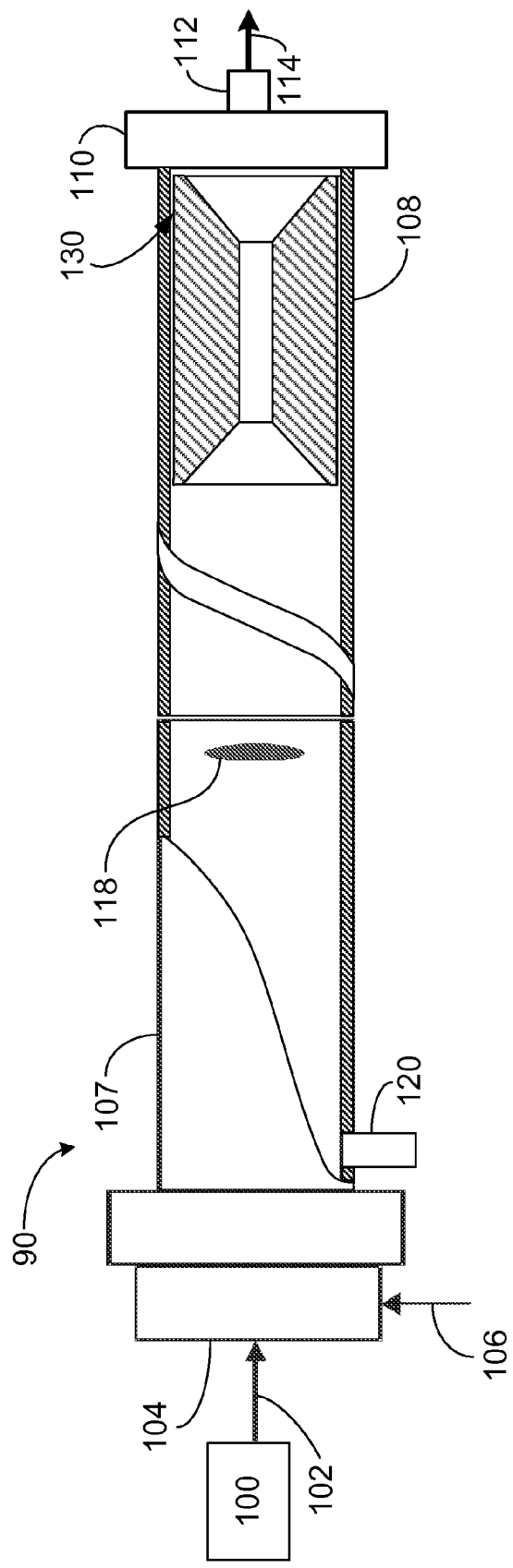
FIG. 8 is a schematic of an ELSD with a flow controller with portions partially broken away to reveal internal construction according to an alternative embodiment of the invention.

Referring now to FIG. 8, in an alternative embodiment of the invention the flow controller 130 is positioned generally at the exit of drift tube 108 adjacent the detection cell 110 and directly before it in the stream. This embodiment reduces droplet splitting that might be cause by flow controller 130 because of the much smaller droplet size after evaporation in the drift tube 108. Advantageously, reducing droplet splitting consequently eliminates signal reduction. The effectiveness of the configuration is similar to the embodiments described above with respect to the examples.

Figure 9:
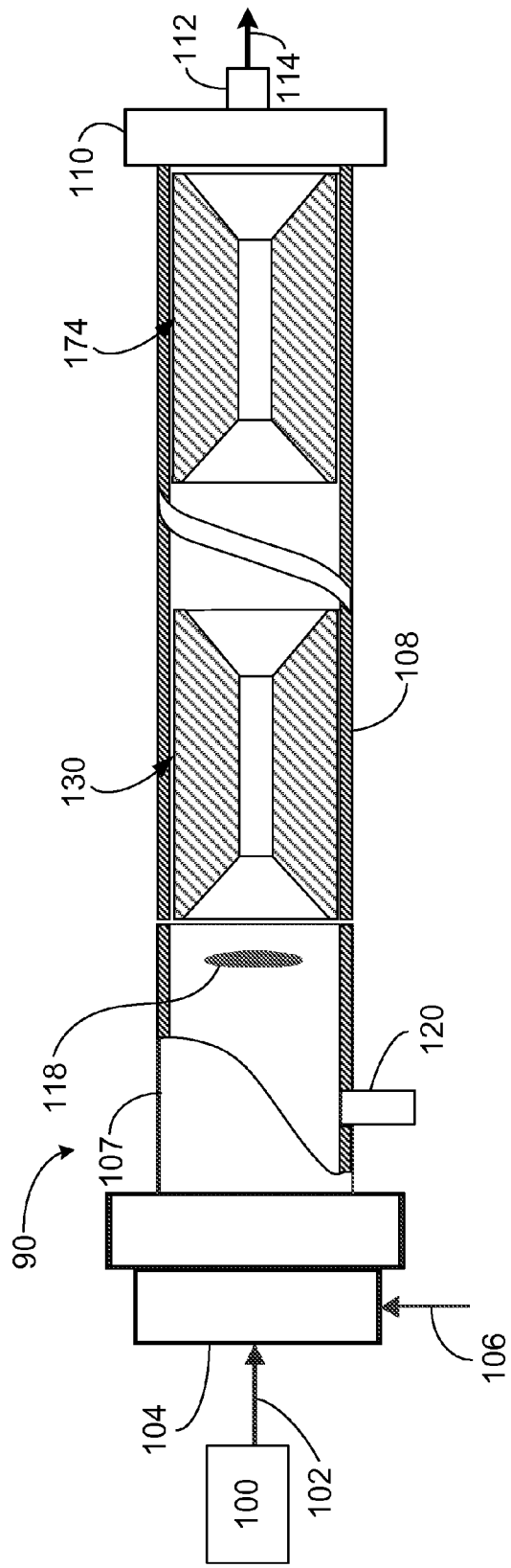
FIG. 9 is a schematic of an ELSD with two flow controllers with portions partially broken away to reveal internal construction according to another alternative embodiment of the invention.

FIG. 9 illustrates another alternative embodiment of the invention in which the flow controller 130 (i.e., a first flow controller) is positioned generally at the entrance of drift tube 108 adjacent the impactor 118 and directly following it in the stream. Another flow controller 174 (i.e., a second flow controller) is positioned generally at the exit of drift tube 108 adjacent the detection cell 110 and directly before it in the stream. This embodiment improves efficiency by removing peak splitting.

When introducing elements of the present invention or the embodiment(s) thereof, the articles "a," "an," "the," and "said" are intended to mean that there are one or more of the elements. The terms "comprising," "including," and "having" are intended to be inclusive and mean that there may be additional elements other than the listed elements.

As various changes could be made in the above products and methods without departing from the scope of the invention, it is intended that all matter contained in the above description and shown in the accompanying drawings shall be interpreted as illustrative and not in a limiting sense.

What is claimed is:

1. A liquid chromatography detector comprising:
    a nebulizer producing droplets for analysis;
    a detection cell adapted for receiving the droplets produced by the nebulizer for analysis by the detection cell;
    a drift tube arranged between the nebulizer and the detection cell adapted for guiding the droplets from the nebulizer to the detection cell as a droplet stream through the drift tube;
    a flow controller arranged between the nebulizer and the detection cell and in communication with the drift tube for receiving the droplet stream, said flow controller comprising a flow channel having a cross-sectional area smaller than a cross-sectional area of the drift tube for channeling the flow of the droplet stream through the smaller cross-sectional area, said flow controller being shaped and sized to reduce turbulence in the droplet stream received by the detection cell; and
    an impactor adapted to intercept droplets larger than a particular size before the droplet stream enters the flow controller, said impactor including a disc generally perpendicular to the flow of the droplet stream and a tube extending generally perpendicular to the disc for intercepting a portion of the mobile phase as it passes through the liquid chromatography detector.

2. A liquid chromatography detector as set forth in claim 1 wherein a distal end of said tube faces the nebulizer.

3. A liquid chromatography detector as set forth in claim 2 wherein said distal end of the tube facing the nebulizer is roughened.

4. A liquid chromatography detector as set forth in claim 1 wherein said tube extends generally perpendicular to the center of the disc for intercepting a central portion of the mobile phase as it passes through the liquid chromatography detector.

5. A liquid chromatography detector as set forth in claim 1 further comprising a nebulizing cartridge between the nebulizer and the drift tube for receiving the droplets produced by the nebulizer, said nebulizing cartridge receiving the impactor, wherein the tube of the impactor extends from the disc between about 1 and about 1.5 times the diameter of the nebulizing cartridge.

6. A liquid chromatography detector as set forth in claim 5 wherein the tube has an inner diameter of between about 20 percent and about 25 percent of the diameter of the nebulizing cartridge.

7. A liquid chromatography detector as set forth in claim 1 wherein the disc is formed from a chemically-stable material with low heat capacity and the tube is formed from a metal.

8. A liquid chromatography detector as set forth in claim 1 wherein said cross-sectional area of the flow channel is between about 2 percent and about 20 percent of the cross-sectional area of the drift tube.

9. A liquid chromatography detector as set forth in claim 1 wherein said cross-sectional area of the flow channel is between about 3 percent and about 10 percent of the cross-sectional area of the drift tube.

10. A liquid chromatography detector as set forth in claim 1 wherein said cross-sectional area of the flow channel is about 5 percent of the cross-sectional area of the drift tube.

11. A liquid chromatography detector as set forth in claim 1 wherein said flow channel of said flow controller includes an inlet portion in communication with the drift tube for receiving the droplet stream and a control channel portion in communication with said inlet portion for channeling the flow of the droplet stream, said control channel portion having said cross-sectional area smaller than the cross-sectional area of the drift tube.

12. A liquid chromatography detector as set forth in claim 11 wherein said inlet portion comprises a tapered inlet sidewall extending from an open mouth of the flow controller and narrowing to the size and shape of the cross-section of the control channel portion.

13. A liquid chromatography detector as set forth in claim 12 wherein said tapered inlet sidewall is substantially conical in shape.

14. A liquid chromatography detector as set forth in claim 13 wherein said tapered inlet sidewall extends at an angle $\alpha$ measured between opposite sides of the tapered inlet sidewall, said angle $\alpha$ being between about 30 degrees and about 120 degrees.

15. A liquid chromatography detector as set forth in claim 14 wherein said angle $\alpha$ is one of about 30 degrees, about 60 degrees, about 82 degrees, about 90 degrees, about 100 degrees, about 110 degrees, and about 120 degrees.

16. A liquid chromatography detector as set forth in claim 11 wherein said control channel portion comprises a generally cylindrical passage.

17. A liquid chromatography detector as set forth in claim 16 wherein said generally cylindrical passage is substantially circular.

18. A liquid chromatography detector as set forth in claim 11 wherein a ratio of the length L of the control channel portion to the width W of the control channel portion is between about 1.5 and about 20.

19. A liquid chromatography detector as set forth in claim 18 wherein the ratio of the length L of the control channel portion to the width W of the control channel portion is between about 2 and about 5.

20. A liquid chromatography detector as set forth in claim 11 wherein said flow channel of said flow controller further comprises an outlet portion in communication with said control channel portion, said outlet portion including a tapered outlet sidewall extending from the cross-section of the control channel portion to an open exit of the flow controller in communication with the detection cell.

21. A liquid chromatography detector as set forth in claim 20 wherein said tapered outlet sidewall is substantially conical in shape.

22. A liquid chromatography detector as set forth in claim 21 wherein said tapered outlet sidewall extends at an angle $\beta$ measured between opposite sides of the tapered outlet sidewall, said angle $\beta$ being between about 30 degrees and about 120 degrees.

23. A liquid chromatography detector as set forth in claim 22 wherein said angle $\beta$ is one of about 30 degrees, about 60 degrees, about 82 degrees, about 90 degrees, about 100 degrees, about 110 degrees, and about 120 degrees.

24. A liquid chromatography detector as set forth in claim 1 wherein a size of said impactor may be reduced to reduce the number of droplets intercepted by the impactor.

25. A liquid chromatography detector as set forth in claim 1 further comprising an outlet drain for draining the intercepted droplets.

26. A liquid chromatography detector as set forth in claim 25 further comprising a drain channel formed along an underside of the flow controller for allowing liquid accumulated between the flow controller and the detection cell to flow past the flow controller to the outlet drain.

27. A liquid chromatography detector as set forth in claim 26 wherein said disc of the impactor comprises a notch whereby said accumulated liquid can flow past the impactor to the outlet drain.

28. A liquid chromatography detector as set forth in claim 1 where said drift tube is adapted for receiving a carrier gas for carrying at least a portion of the droplets as the droplet stream from the nebulizer to the detection cell through the drift tube.

29. A liquid chromatography detector comprising:
a drift tube adapted for guiding nebulized droplets as a droplet stream;
a flow controller arranged within the drift tube, said flow controller comprising a flow channel having a cross-sectional area smaller than a cross-sectional area of the drift tube for channeling the droplet stream through the smaller cross-sectional area, said flow controller being shaped and sized to reduce turbulence in the droplet stream; and
an impactor adapted to intercept droplets larger than a particular size before the droplet stream enters the flow controller, said impactor including a disc generally perpendicular to the flow of the droplet stream and a tube extending generally perpendicular to the disc for intercepting a portion of the mobile phase as it passes through the liquid chromatography detector.

30. A liquid chromatography detector comprising:

a nebulizer producing droplets for analysis;

a detector adapted for analyzing said droplets;

a drift tube shaped and sized for guiding the droplets from the nebulizer to the detector, said drift tube having a cross-sectional area;

a flow controller arranged between the nebulizer and the detector for receiving the droplet stream, said flow controller comprising a flow channel having a cross-sectional area smaller than a cross-sectional area of the drift tube; and an impactor adapted to intercept droplets larger than a particular size before the droplet stream enters the flow controller, said impactor including a disc generally perpendicular to the flow of the droplet stream and a tube extending generally perpendicular to the disc for intercepting a portion of the mobile phase as it passes through the liquid chromatography detector.

* * * * *

UNITED STATES PATENT AND TRADEMARK OFFICE
CERTIFICATE OF CORRECTION

| | |
|---|---|
| PATENT NO. | : 8,397,553 B2 |
| APPLICATION NO. | : 12/517946 |
| DATED | : March 19, 2013 |
| INVENTOR(S) | : Xu et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 954 days.

Signed and Sealed this
Twentieth Day of August, 2013

Teresa Stanek Rea
*Acting Director of the United States Patent and Trademark Office*